United States Patent
Takasugi et al.

(10) Patent No.: US 6,235,762 B1
(45) Date of Patent: May 22, 2001

(54) 2-ARYL-$\Delta^2$-1,3,4-(OXA AND THIA) DIAZOLINE INSECTICIDAL AND ACARICIDAL AGENTS

(75) Inventors: James Jan Takasugi, Lawrenceville, NJ (US); Brian Lee Buckwalter, Yardley, PA (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/435,343

(22) Filed: Nov. 5, 1999

Related U.S. Application Data

(60) Provisional application No. 60/109,448, filed on Nov. 23, 1998.

(51) Int. Cl.$^7$ .................. A01N 47/34; A01N 285/12; A01N 271/10
(52) U.S. Cl. .................. 514/363; 514/364; 548/136; 548/143
(58) Field of Search .................... 548/136, 143; 514/363, 364

(56) References Cited

U.S. PATENT DOCUMENTS 5,670,456  9/1997  Anderson et al. .

OTHER PUBLICATIONS

D. Kochetov et al., Ukrainskii Khimicheskii Zhurnal, 57(2), 215–217 (1991).

Matsubara et al., "Synthesis of Novel 2–substituted–1,3, 4–thiadiazoles" Chem. Pharm. Bull. 46 329–331 (1998).

Matsubara Chem Pharm Bull 46 (2) 329–31Feb. 1998, Abstract.*

* cited by examiner

*Primary Examiner*—Robert Gerstl
(74) *Attorney, Agent, or Firm*—Charles F. Costello

(57) ABSTRACT

The present invention relates to 2-aryl-$\Delta^2$-1,3,4-(oxa and thia)diazoline compounds having the structural formula

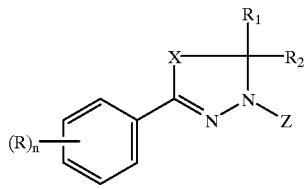

and compositions and methods comprising those compounds for the control of insect and acarid pests.

16 Claims, No Drawings

2-ARYL-Δ²-1,3,4-(OXA AND THIA) DIAZOLINE INSECTICIDAL AND ACARICIDAL AGENTS

This application claims priority from copending provisional application(s) Ser. No. 60/109,448 filed on Nov. 23, 1998.

BACKGROUND OF THE INVENTION

Insect and acarid pests destroy growing and harvested crops. In the United States, agronomic crops must compete with thousands of those pests. In particular, tobacco budworms and southern armyworms are especially devastating to crops.

Tobacco budworms cause tremendous economic losses in agronomic crops. In particular, budworms devastate cotton crops by feeding on green bolls. Control of budworms is complicated by their resistance to many common insecticides, including organophosphates, carbamates and pyrethroids.

In spite of the commercial insecticides and acaricides available today, damage to crops, both growing and harvested, caused by insect and acarid pests still occurs. Accordingly, there is ongoing research to create new and more effective insecticidal and acaricidal agents.

Certain N-carbamoyl-3-carboxyaryl-heterocyclic and hydrazinecarboximidamidohydrazone compounds which are useful as herbicidal agents are described in U.S. Pat. No. 5,670,456. However, that patent does not describe any insecticidal or acaricidal activity.

Certain cyclic 1,3,4-oxadiazoline compounds are described by D. Kochetov et al in Ukrainskii Khimicheskii Zhurnal, 57(2), pp. 215–217 (1991). However, D. Kochetov et al do not disclose any utility for their cyclic 1,3,4-oxadiazoline compounds It is, therefore, an object of the present invention to provide compounds which are useful for the control of insect and acarid pests.

It is also an object of the present invention to provide a method for the control of insect and acarid pests.

It is a further object of this invention to provide a method for the protection of growing and harvested crops from damage caused by insect and acarid attack and infestation.

These and other objects of the present invention will become more apparent from the description thereof set forth below.

SUMMARY OF THE INVENTION

The present invention comprises 2-aryl-Δ²-1,3,4-(oxa and thia)diazoline compounds which are useful for the control of insect and acarid pests. Those compounds are also useful for protecting plants from damage caused by insect and acarid attack and infestation.

The pesticidal 2-aryl-Δ²-1,3,4-(oxa and thia)diazoline compounds of the present invention have the structural formula I

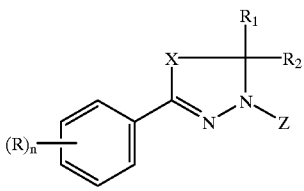

(I)

wherein
X is O or $S(O)_m$;
Z is

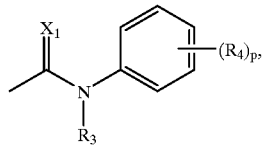

$C(X_1)R_5$, $C_1$–$C_6$alkyl, $C_1$–$C_6$haloalkyl,
benzyl optionally substituted on the phenyl ring with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkyl-thio groups, or
phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups,
provided that when X is O, Z is

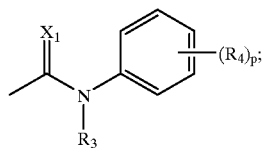

n and p are each independently 0, 1, 2 or 3;
$X_1$ is O or S;
R and $R_4$ are each independently halogen, $C_1$–$C_6$alkyl, $C_1$–$C_6$haloalkyl, $OR_6$, $S(O)_qR_7$, nitro, cyano, $NR_8R_9$, $CO_2R_{10}$, $C(O)R_{11}$ or
phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, or
two adjacent R groups or $R_4$ groups may be taken together to form a ring wherein RR or $R_4R_4$ is represented by: —$OCH_2O$—, —$OCF_2O$— or —CH=CH—CH=CH—;
$R_6$ and $R_7$ are each independently hydrogen, $C_1$–$C_6$alkyl, $C_1$–$C_6$haloalkyl or
phenyl optionally substituted with any combination of from one to three halogen, $C_1$–$C_6$alkyl, $C_1$–$C_6$haloalkyl, $C_1$–$C_6$alkoxy, $C_1$–$C_4$haloalkoxy, $C_1$–$C_6$alkylthio or $C_1$–$C_6$haloalkylthio groups;
$R_8$, $R_9$, $R_{13}$ and $R_{14}$ are each independently hydrogen, $C_1$–$C_6$alkyl, $C_1$–$C_6$alkylcarbonyl or
phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups;

$R_{10}$ and $R_{11}$ are each independently hydrogen, $C_1$–$C_6$alkyl or $C_1$–$C_6$haloalkyl;

$R_1$ and $R_2$ are each independently hydrogen, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_2$–$C_6$alkoxyalkyl, $(CH_2)_vC(O)R_{12}$, $C_1$–$C_6$alkyl optionally substituted with one phenoxy or phenyl group wherein the phenyl ring of each group is independently, optionally substituted with from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, phenyl optionally substituted with from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, or a 5- or 6-membered heteroaromatic ring optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, and when $R_1$ and $R_2$ are taken together with the atom to which they are attached they may form a $C_3$–$C_6$cycloalkyl ring wherein $R_1R_2$ is represented by: —$(CH_2)_t$— where t is 2, 3, 4 or 5;

m, q and v are each independently 0, 1 or 2;

$R_{12}$ is hydrogen, $C_1$–$C_6$alkyl, $C_1$–$C_6$haloalkyl, $C_1$–$C_6$alkoxy, $C_1$–$C_6$haloalkoxy, $C_1$–$C_6$alkylthio, $C_1$–$C_6$haloalkylthio or $NR_{13}R_{14}$;

$R_3$ is hydrogen, $C_1$–$C_6$alkyl, $C_1$–$C_6$haloalkyl or $C(O)R_{15}$;

$R_{15}$ is $C_1$–$C_6$alkyl, $C_1$–$C_6$haloalkyl, $C_1$–$C_6$alkoxy or $C_1$–$C_6$haloalkoxy; and $R_5$ is $C_1$–$C_6$alkyl, phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, or benzyl optionally substituted on the phenyl ring with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups; and the optical isomers thereof and the agriculturally acceptable salts thereof.

DETAILED DESCRIPTION OF THE INVENTION

The present invention provides a method for the control of insect or acarid pests which comprises contacting said pests or their food supply, habitat or breeding grounds with a pesticidally effective amount of a 2-aryl-$\Delta^2$-1,3,4-(oxa or thia)diazoline compound of formula I.

The present invention also provides a method for the protection of growing plants from attack or infestation by insect or acarid pests which comprises applying to the foliage of the plants, or to the soil or water in which they are growing, a pesticidally effective amount of a 2-aryl-$\Delta^2$-1,3,4-(oxa or thia)diazoline compound of formula I The pesticidal 2-aryl-$\Delta^2$-1,3,4-(oxa and thia)diazoline compounds of the present invention have the structural formula I

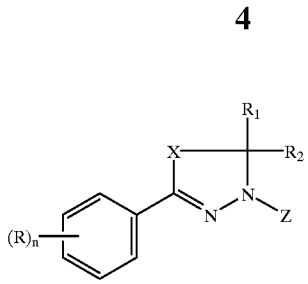

(I)

wherein n, R, $R_1$, $R_2$, X and Z are as described hereinabove for formula I.

Preferred 2-aryl-$\Delta^2$-1,3,4-oxadiazoline compounds of the present invention are those having the structural formula II

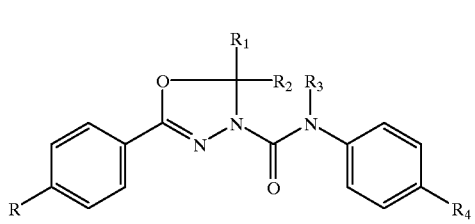

(II)

wherein

R is halogen, $C_1$–$C_4$haloalkyl, $C_1$–$C_4$haloalkoxy or phenoxy optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

$R_4$ is $C_1$–$C_4$haloalkyl, $C_1$–$C_4$haloalkoxy or $C_1$–$C_4$haloalkylthio;

$R_1$ is $C_1$–$C_4$alkyl;

$R_2$ is $C_1$–$C_4$alkyl, $C_1$–$C_4$haloalkyl, $(CH_2)_vC(O)R_{12}$ or 2-pyridyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

v is 0 or 1;

$R_{12}$ is $C_1$–$C_4$alkoxy or $C_1$–$C_4$haloalkoxy;

$R_3$ is hydrogen or $C(O)R_{15}$; and $R_{15}$ is $C_1$–$C_4$alkoxy.

More preferred insecticidal and acaricidal agents of the present invention are those having the structural formula II wherein R is F, Br, Cl or phenoxy;

$R_4$ is $CF_3$, $OCF_3$ or $SCF_3$;

$R_1$ is $CH_3$;

$R_2$ is $CH_3$, $CH_2Cl$, $CH_2CF_3$, $CF_3$, $CH_2CO_2CH_3$ or 2-pyridyl; and $R_3$ is hydrogen or $CO_2CH_3$.

Compounds of this invention which are particularly effective insecticidal agents include 2-(p-chlorophenyl)-5,5-dimethyl-4'-(trifluoromethoxy)-$\Delta^2$-1,3,4-oxadiazoline-4-carboxanilide;

2-(p-chlorophenyl)-5,5-dimethyl-4'-(trifluoromethyl)-$\Delta^2$-1,3,4-oxadiazoline-4-carboxanilide;

2-(p-bromophenyl)-5,5-dimethyl-4'-(trifluoromethyl)-$\Delta^2$-1,3,4-oxadiazoline-4-carboxanilide;

2-(p-fluorophenyl)-5,5-dimethyl-4'-(trifluoromethyl)-$\Delta^2$-1,3,4-oxadiazoline-4-carboxanilide;

5,5-dimethyl-2-(p-phenoxyphenyl)-4'-[(trifluoromethyl)thio]-$\Delta^2$-1,3,4-oxadiazoline-4-carboxanilide;

2-(p-chlorophenyl)-5-methyl-4'-(trifluoromethoxy)-5-(trifluoromethyl)-Δ²-1,3,4-oxadiazoline-4-carboxanilide;

5-(chloromethyl)-2-(p-chlorophenyl)-5-methyl-4'-(trifluoromethyl)-Δ²-1,3,4-oxadiazoline-4-carboxanilide;

4,5-bis(trifluoromethyl)-2-(p-fluorophenyl)-5-methyl-Δ²-1,3,4-oxadiazoline-4-carboxanilide;

5-(chloromethyl)-2-(p-fluorophenyl)-5-methyl-4'-(trifluoromethyl)-Δ²-1,3,4-oxadiazoline-4-carboxanilide;

5-(chloromethyl)-2-(p-fluorophenyl)-5-methyl-4'-(trifluoromethoxy)-Δ²-1,3,4-oxadiazoline-4-carboxanilide;

2-(p-bromophenyl)-5-(chloromethyl)-5-methyl-4'-(trifluoromethoxy)-Δ²-1,3,4-oxadiazoline-4-carboxanilide;

2-(p-chlorophenyl)-5-methyl-5-(2,2,2-trifluoroethyl)-4'-(trifluoromethyl)-Δ²-1,3,4-oxadiazoline-4-carboxanilide;

2-(p-chlorophenyl)-5-methyl-5-(2,2,2-trifluoroethyl)-4'-(trifluoromethoxy)-Δ²-1,3,4-oxadiazoline-4-carboxanilide;

2-(p-chlorophenyl)-5-methyl-5-(2-pyridyl)-4'-(trifluoromethyl)-Δ²-1,3,4-oxadiazoline-4-carboxanilide;

2-(p-chlorophenyl)-5-methyl-5-(2-pyridyl)-4'-(trifluoromethoxy)-Δ²-1,3,4-oxadiazoline-4-carboxanilide;

methyl N-{[2-(p-chlorophenyl)-5,5-dimethyl-Δ²-1,3,4-oxadiazolin-4-yl]carbonyl}-p-(trifluoromethoxy)-carbanilate;

methyl N-{[2-(p-chlorophenyl)-5,5-dimethyl-Δ²-1,3,4-oxadiazolin-4-yl]carbonyl}-p-(trifluoromethyl)-carbanilate; and methyl 2-(p-chlorophenyl)-5-methyl-4-{[p-(trifluoromethoxy)phenyl]carbamoyl}-Δ²-1,3,4-oxadiazoline-5-acetate, among others.

In formula I above, 5- and 6-membered heteroaromatic rings include, but are not limited to, pyridyl, pyrazolyl, imidazolyl, triazolyl, isoxazolyl, tetrazolyl, pyrazinyl, pyridazinyl, triazinyl, furanyl, thienyl, and thiazolyl rings each optionally substituted as described in formula I above.

Exemplary of halogen hereinabove are fluorine, chlorine, bromine and iodine. The terms "$C_1$–$C_6$haloalkyl", "$C_1$–$C_4$haloalkyl", "$C_1$–$C6$ haloalkoxy", "$C_1$–$C_4$haloalkoxy", "$C_1$–$C_6$haloalkylthio" and "$C_1$–$C_4$haloalkylthio" are defined as a $C_1$–$C_6$alkyl group, a $C_1$–$C_4$alkyl group, a $C_1$–$C_6$alkoxy group, a $C_1$–$C_4$alkoxy group, a $C_1$–$C_6$alkylthio group and a $C_1$–$C_4$alkylthio group substituted with one or more halogen atoms, respectively.

Novel 2-aryl-Δ²-1,3,4-(oxa and thia)diazoline compounds of the present invention are those having the structural formula I

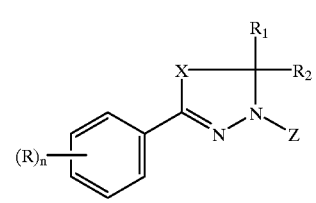

wherein n, R, $R_1$, $R_2$, X and Z are as described hereinabove, provided that: (1) R is other than $CO_2R_{10}$ when R is on the ortho-position of the phenyl ring, and (2) $R_2$ is other than ethyl or unsubstituted phenyl when X is O, n and p are 0 and $R_1$ is methyl.

Formula I compounds wherein X is O and

Z is

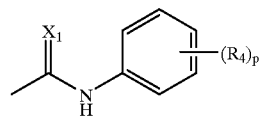

may be prepared, as illustrated in Flow Diagram I, by reacting a hydrazine of formula III with a ketone of formula IV in the presence of a solvent such as acetone, ethanol, methylene chloride, 1,1-diethoxyethane and the like, preferably at an elevated temperature, to form a hydrazone of formula V, and reacting the formula V hydrazone with an isocyanate or isothiocyanate of formula VI in the presence of a solvent such as 1,2-dichloroethane and ethyl acetate, preferably at an elevated temperature.

FLOW DIAGRAM I

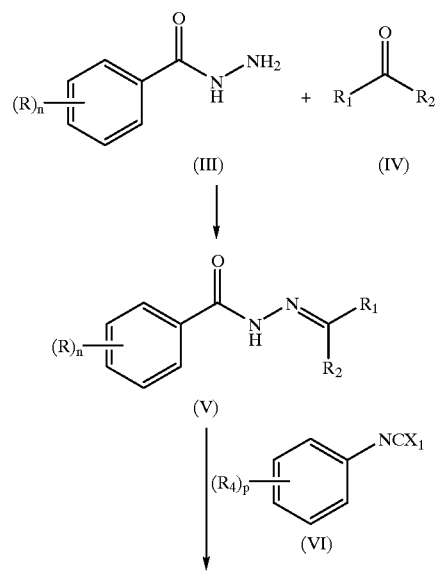

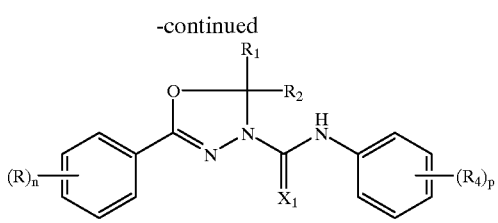

Alternatively, formula I compounds wherein X is O, $R_1$ is methyl, $R_2$ is $C_1$–$C_6$haloalkyl and Z is

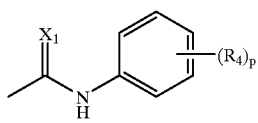

may be prepared, as shown in Flow Diagram II, by reacting a hydrazine of formula III with a 1-haloalkyl-1-acetoxyethylene compound of formula VII in the presence of a solvent such as ethanol, preferably at an elevated temperature, to obtain a hydrazone of formula VIII, and reacting the formula VIII hydrazone with an isocyanate or isothiocyanate of formula VI in the presence of a solvent such as 1,2-dichloroethane and ethyl acetate, preferably at an elevated temperature.

Formula I compounds wherein X is S and

Z is

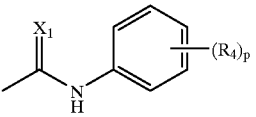

may be prepared, as illustrated in Flow Diagram III, by reacting a hydrazine of formula IX with a ketone of formula IV in the presence of a solvent such as acetone, ethanol, methylene chloride, 1,1-diethoxyethane and the like to form a 2-aryl-$\Delta^2$-1,3,4-thiadiazoline of formula X, and reacting the formula X compound with an isocyanate or isothiocyanate of formula VI in the presence of a solvent such as 1,2-dichlorethane and ethyl acetate.

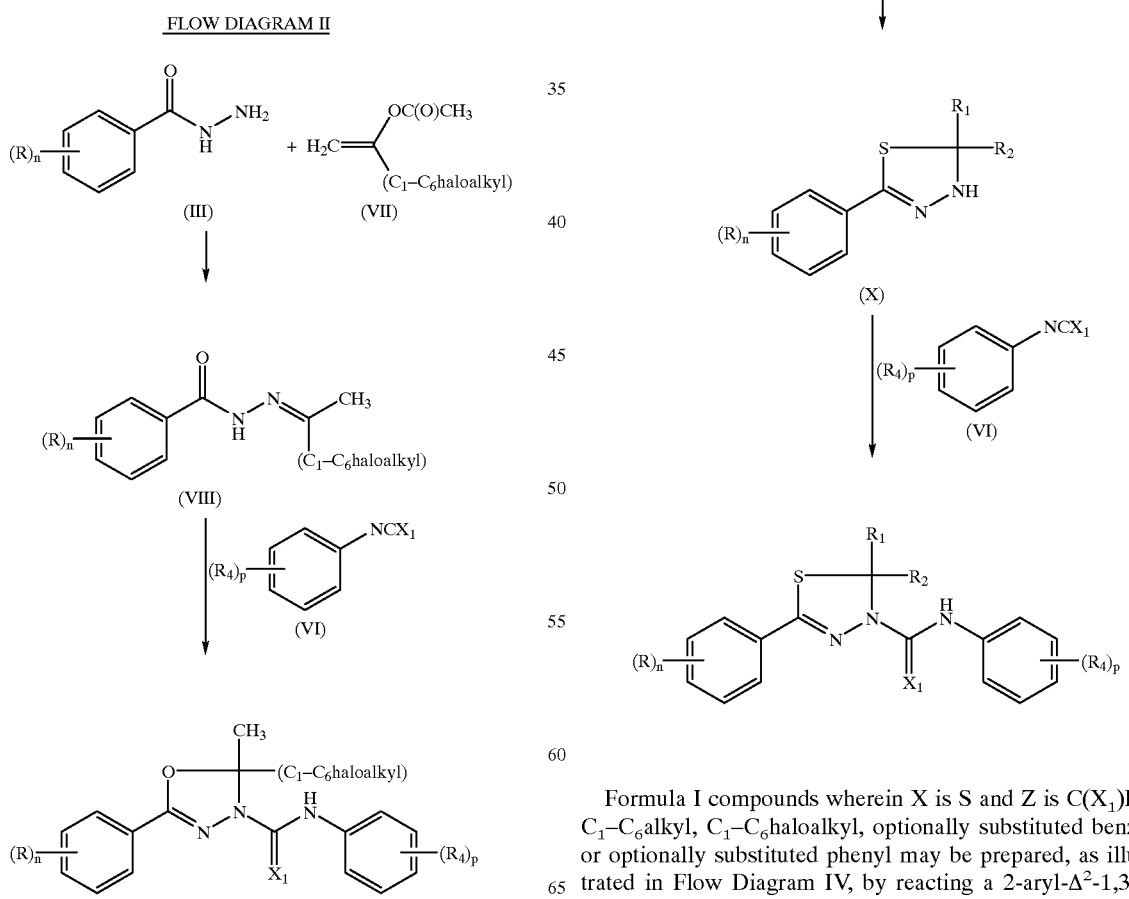

FLOW DIAGRAM II

FLOW DIAGRAM III

Formula I compounds wherein X is S and Z is $C(X_1)R_5$, $C_1$–$C_6$alkyl, $C_1$–$C_6$haloalkyl, optionally substituted benzyl or optionally substituted phenyl may be prepared, as illustrated in Flow Diagram IV, by reacting a 2-aryl-$\Delta^2$-1,3,4-thiadiazoline of formula X with a halide compound of formula XI and a base in the presence of a solvent.

FLOW DIAGRAM IV

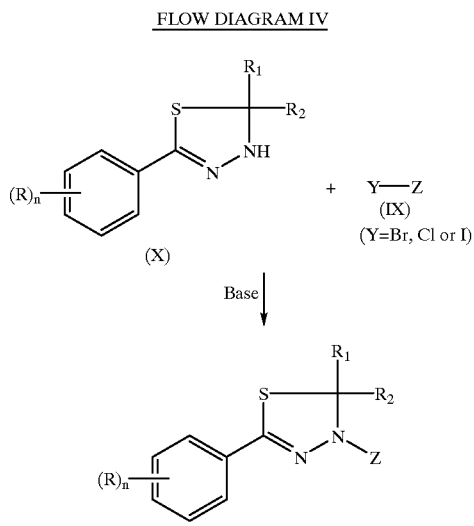

In addition, certain compounds of formula I may be converted into other compounds of formula I by using conventional procedures known to those skilled in the art.

The 2-aryl-$\Delta^2$-1,3,4-(oxa and thia)diazoline compounds of the present invention are effective for controlling insect and acarid pests. Those compounds are also effective for protecting growing or harvested crops from damage caused by insect and acarid attack and infestation.

Insects controlled by the a 2-aryl-$\Delta^2$-1,3,4-(oxa and thia)diazoline compounds of this invention include Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips; Coleoptera such as boll weevils, Colorado potato beetles, southern corn rootworms, western corn rootworms and mustard beetles; and Orthoptera such as locusts, crickets, grasshoppers and cockroaches. Acarina controlled by the compounds of this invention include mites such as two-spotted spider mites, carmine spider mites, banks grass mites, strawberry mites, citrus rust mites and leprosis mites.

In practice generally about 10 ppm to about 10,000 ppm and preferably about 100 ppm to about 5,000 ppm of a formula I compound, dispersed in water or another liquid carrier, is effective when applied to plants or the soil in which the plants are growing to protect the plants from insect and acarid attack and infestation.

The 2-aryl-$\Delta^2$-1,3,4-(oxa and thia)diazoline compounds of this invention are also effective for controlling insect and acarid pests when applied to the foliage of plants and/or to the soil or water in which said plants are growing in sufficient amount to provide a rate of about 0.1 kg/ha to 4.0 kg/ha of active ingredient.

While the compounds of this invention are effective for controlling insect and acarid pests when employed alone, they may also be used in combination with other biological agents, including other insecticides and acaricides. For example, the formula I compounds of this invention may be used effectively in conjunction or combination with pyrethroids, phosphates, carbamates, cyclodienes, endotoxin of *Bacillus thuringiensis* (Bt), formamidines, phenol tin compounds, chlorinated hydrocarbons, benzoylphenylureas, pyrroles and the like.

The compounds of this invention may be formulated as emulsifiable concentrates, flowable concentrates or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations or compositions of the present invention include a compound of the invention (or combinations thereof) admixed with one or more agronomically acceptable inert, solid or liquid carriers. Those compositions contain a pesticidally effective amount of said compound or compounds, which amount may vary depending upon the particular compound, target pest, and method of use. Those skilled in the art can readily determine what is a pesticidally effective amount without undue experimentation.

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Preparation of 2-($\alpha,\alpha,\alpha$-Trifluoro-m-tolyl)-5,5-dimethyl-4'-(trifluoromethoxy)-$\Delta^2$-1,3,4-oxadiazoline-4-carboxanilide

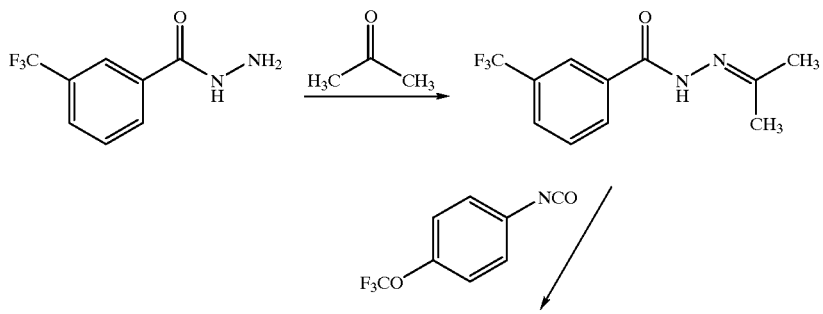

-continued

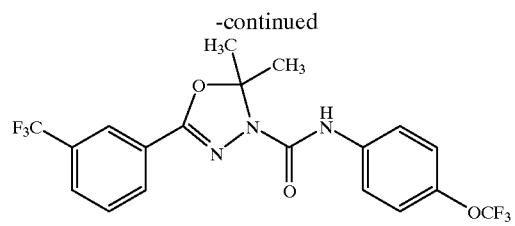

A solution of m-trifluoromethylbenzoyl hydrazine (1.84 g) and acetone (40 mL) is refluxed for 48 hours, cooled to room temperature and concentrated in vacuo to obtain a colorless hydrazone (1.48 g, m.p. 100–103° C.). A solution of the hydrazone (0.74 g), p-trifluoromethoxyphenylisocyanate (0.62 g), and 1,2-dichloroethane (15 mL) is refluxed for 16 hours, cooled to room temperature, and concentrated in vacuo to give the title product as a colorless solid (1.28 g, m.p. 120–122° C.).

Using essentially the same procedure as described for the preparation of Example 1, but using the appropriately substituted hydrazine, ketone and isocyanate, the following compounds are obtained:

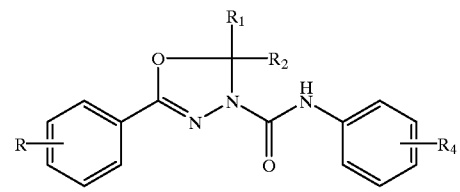

| Example | R | $R_1$ | $R_2$ | $R_4$ | mp ° C. |
|---|---|---|---|---|---|
| 2 | 4-Cl | $CH_3$ | $CH_3$ | 4-$OCF_3$ | 100–105 |
| 3 | 4-Cl | $CH_3$ | $CH_3$ | 4-$CF_3$ | 136–137 |
| 4 | 4-Cl | $CH_3$ | $CH_3$ | 4-F | 168–169 |
| 5 | 4-Cl | $CH_3$ | $CH_3$ | 4-Cl | 169–170 |
| 6 | 4-$CF_3$ | $CH_3$ | $CH_3$ | 4-$OCF_3$ | 121–122 |
| 7 | 4-$CF_3$ | $CH_3$ | $CH_3$ | 4-$CF_3$ | 136–137 |
| 8 | 3-$CF_3$ | $CH_3$ | $CH_3$ | 4-$CF_3$ | 156–158 |
| 9 | 4-Cl | $CH_3$ | $CH_3$ | 4-$SCF_3$ | 142–143 |
| 10 | 4-Cl | $CH_3$ | $CH_3$ | 4-Br | |
| 11 | 4-Cl | $CH_3$ | $CH_3$ | 3-I | |
| 12 | 4-Cl | $CH_3$ | $CH_3$ | 4-I | |
| 13 | 4-Cl | $CH_3$ | $CH_3$ | 3-$CF_3$ | |
| 14 | 4-Cl | $CH_3$ | $CH_3$ | 4-CN | |
| 15 | 4-Cl | $CH_3$ | $CH_3$ | 3-$CH_3$ | |
| 16 | 4-Cl | $CH_3$ | $CH_3$ | 4-$CO_2C_2H_5$ | |
| 17 | 4-Cl | $CH_3$ | $CH_3$ | 4-$C_6H_5$ | |
| 18 | 4-Cl | $CH_3$ | $CH_3$ | 2,5-di-$CH_3$ | |
| 19 | 4-Cl | $CH_3$ | $CH_3$ | 4-$CH_2Cl$ | |
| 20 | 4-Cl | $CH_3$ | $CH_3$ | 3,5-di-$CF_3$ | |
| 21 | 4-Cl | $CH_3$ | $CH_3$ | 2,3-(CH=CHCH=CH) | |
| 22 | 4-Cl | $CH_3$ | $CH_3$ | 2,4-di-Cl | |
| 23 | 2,4-di-F | $CH_3$ | $CH_3$ | 4-Cl | |
| 24 | 4-Cl | $CH_3$ | $CH_3$ | 2,6-di-F | |
| 25 | 4-Cl | $CH_3$ | $CH_3$ | 3-Cl-4-F | |
| 26 | 4-Cl | $CH_3$ | $CH_3$ | 3,4-di-F | |
| 27 | 4-Br | $CH_3$ | $CH_3$ | 4-$CF_3$ | |
| 28 | 4-F | $CH_3$ | $CH_3$ | 4-$CF_3$ | |
| 29 | 4-$CH_3$ | $CH_3$ | $CH_3$ | 3-$CF_3$ | |
| 30 | 4-$OCH_3$ | $CH_3$ | $CH_3$ | 4-$CF_3$ | |
| 31 | 4-$C_6H_5$ | $CH_3$ | $CH_3$ | 4-$CF_3$ | |
| 32 | 4-$OC_6H_5$ | $CH_3$ | $CH_3$ | 4-$CF_3$ | |
| 33 | 4-$N(CH_3)_2$ | $CH_3$ | $CH_3$ | 4-$CF_3$ | |
| 34 | 4-I | $CH_3$ | $CH_3$ | 4-$CF_3$ | |
| 35 | 4-Br | $CH_3$ | $CH_3$ | 4-$OCF_3$ | |
| 36 | 4-F | $CH_3$ | $CH_3$ | 4-$OCF_3$ | |
| 37 | 4-$CH_3$ | $CH_3$ | $CH_3$ | 4-$OCF_3$ | |
| 38 | 4-$OCH_3$ | $CH_3$ | $CH_3$ | 4-$OCF_3$ | |
| 39 | 4-$C_6H_5$ | $CH_3$ | $CH_3$ | 4-$OCF_3$ | |
| 40 | 4-$OC_6H_5$ | $CH_3$ | $CH_3$ | 4-$OCF_3$ | |
| 41 | 4-$N(CH_3)_2$ | $CH_3$ | $CH_3$ | 4-$OCF_3$ | |
| 42 | 4-t-Butyl | $CH_3$ | $CH_3$ | 4-$OCF_3$ | |
| 43 | 4-I | $CH_3$ | $CH_3$ | 4-$OCF_3$ | |
| 44 | H | $CH_3$ | $CH_3$ | 4-$CF_3$ | |

-continued

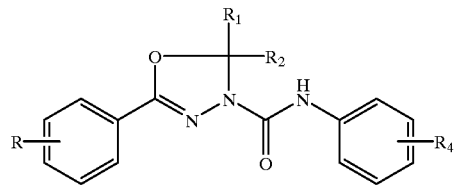

| Example | R | $R_1$ | $R_2$ | $R_4$ | mp °C. |
|---|---|---|---|---|---|
| 45 | 3,4-(CH=CHCH=CH) | $CH_3$ | $CH_3$ | 4-$CF_3$ | |
| 46 | 3,4-di-Cl | $CH_3$ | $CH_3$ | 4-$CF_3$ | |
| 47 | 4-NHC(O)$CH_3$ | $CH_3$ | $CH_3$ | 4-$CF_3$ | |
| 48 | 2,4-di-Cl | $CH_3$ | $CH_3$ | 4-$CF_3$ | |
| 49 | H | $CH_3$ | $CH_3$ | 4-$OCF_3$ | |
| 50 | 3,4-di-Cl | $CH_3$ | $CH_3$ | 4-$OCF_3$ | |
| 51 | 3,4-(OCH$_2$O) | $CH_3$ | $CH_3$ | 4-$OCF_3$ | |
| 52 | 4-NHC(O)$CH_3$ | $CH_3$ | $CH_3$ | 4-$OCF_3$ | |
| 53 | 4-Cl | $CH_3$ | $CH_3$ | 4-$SCF_3$ | |
| 54 | 4-Cl | $CH_3$ | $CH_3$ | 2-Cl | |
| 55 | 4-Cl | $CH_3$ | $CH_3$ | 3-$SCH_3$ | |
| 56 | 4-Cl | $CH_3$ | $CH_3$ | 2-$OCF_3$ | |
| 57 | 4-Cl | $CH_3$ | $CH_3$ | 2,4,6-tri-$CH_3$ | |
| 58 | 4-Cl | $CH_3$ | $CH_3$ | 2,4,6-tri-Cl | |
| 59 | 4-Br | $CH_3$ | $CH_3$ | 4-I | |
| 60 | 4-F | $CH_3$ | $CH_3$ | 4-I | |
| 61 | 4-$CH_3$ | $CH_3$ | $CH_3$ | 4-I | |
| 62 | 4-$OCH_3$ | $CH_3$ | $CH_3$ | 4-I | |
| 63 | 4-$C_6H_5$ | $CH_3$ | $CH_3$ | 4-I | |
| 64 | 4-$OC_6H_5$ | $CH_3$ | $CH_3$ | 4-I | |
| 65 | 4-$N(CH_3)_2$ | $CH_3$ | $CH_3$ | 4-I | |
| 66 | 4-t-Butyl | $CH_3$ | $CH_3$ | 4-I | |
| 67 | 4-I | $CH_3$ | $CH_3$ | 4-I | |
| 68 | 4-Br | $CH_3$ | $CH_3$ | 4-Br | |
| 69 | 4-F | $CH_3$ | $CH_3$ | 4-Br | |
| 70 | 4-$CH_3$ | $CH_3$ | $CH_3$ | 4-Br | |
| 71 | 4-$OCH_3$ | $CH_3$ | $CH_3$ | 4-Br | |
| 72 | 4-$NO_2$ | $CH_3$ | $CH_3$ | 4-Br | |
| 73 | 4-$C_6H_5$ | $CH_3$ | $CH_3$ | 4-Br | |
| 74 | 4-$OC_6H_5$ | $CH_3$ | $CH_3$ | 4-Br | |
| 75 | 4-$N(CH_3)_2$ | $CH_3$ | $CH_3$ | 4-Br | |
| 76 | 4-t-Butyl | $CH_3$ | $CH_3$ | 4-Br | |
| 77 | 4-I | $CH_3$ | $CH_3$ | 4-Br | |
| 78 | 4-Br | $CH_3$ | $CH_3$ | 4-CN | |
| 79 | 4-F | $CH_3$ | $CH_3$ | 4-CN | |
| 80 | 4-$CH_3$ | $CH_3$ | $CH_3$ | 4-CN | |
| 81 | 4-$OCH_3$ | $CH_3$ | $CH_3$ | 4-CN | |
| 82 | 4-$NO_2$ | $CH_3$ | $CH_3$ | 4-CN | |
| 83 | 4-$OC_6H_5$ | $CH_3$ | $CH_3$ | 4-CN | |
| 84 | 4-$N(CH_3)_2$ | $CH_3$ | $CH_3$ | 4-CN | |
| 85 | 4-I | $CH_3$ | $CH_3$ | 4-CN | |
| 86 | 4-Br | $CH_3$ | $CH_3$ | 4-$SCF_3$ | |
| 87 | 4-F | $CH_3$ | $CH_3$ | 4-$SCF_3$ | |
| 88 | 4-$CH_3$ | $CH_3$ | $CH_3$ | 4-$SCF_3$ | |
| 89 | 4-$OCH_3$ | $CH_3$ | $CH_3$ | 4-$SCF_3$ | |
| 90 | 4-$NO_2$ | $CH_3$ | $CH_3$ | 4-$SCF_3$ | |
| 91 | 4-$C_6H_5$ | $CH_3$ | $CH_3$ | 4-$SCF_3$ | |
| 92 | 4-$OC_6H_5$ | $CH_3$ | $CH_3$ | 4-$SCF_3$ | |
| 93 | 4-$N(CH_3)_2$ | $CH_3$ | $CH_3$ | 4-$SCF_3$ | |
| 94 | 4-I | $CH_3$ | $CH_3$ | 4-$SCF_3$ | |
| 95 | 4-Cl | $CH_3$ | $C_6H_5$ | 4-$OCF_3$ | 52–62 |
| 96 | 4-Cl | —$(CH_2)_4$— | | 4-$OCF_3$ | 138–139 |
| 97 | 4-Cl | $CH_3$ | $C_6H_5$ | 4-$CF_3$ | 123–152 |
| 98 | 4-Cl | $CH_3$ | $CO_2CH_3$ | 4-$OCF_3$ | 126–127 |
| 99 | 4-Cl | H | $C_6H_5$ | 4-$OCF_3$ | 216–217 |
| 100 | 4-Cl | $C_6H_5$ | $C_6H_5$ | 4-$OCF_3$ | 122–123 |
| 101 | 4-Cl | H | $CH_2C_6H_5$ | 4-$OCF_3$ | 106–108 |
| 102 | 4-Cl | H | $CH_3$ | 4-$OCF_3$ | 116–118 |
| 103 | 4-Cl | —$(CH_2)_3$— | | 4-$CF_3$ | 167–168 |
| 104 | 4-Cl | H | $CH_3$ | 4-$CF_3$ | 132–133 |
| 105 | 4-Cl | H | $C_6H_5$ | 4-$CF_3$ | 208–210 |
| 106 | 4-Cl | —$(CH_2)_3$— | | 4-$OCF_3$ | 130–131 |
| 107 | 4-Cl | H | $CH_2C_6H_5$ | 4-$CF_3$ | 137–138 |
| 108 | 4-Cl | $CH_3$ | $CO_2CH_3$ | 4-$CF_3$ | 162–163 |
| 109 | 4-Cl | $CH_3$ | $C_2H_5$ | 4-$CF_3$ | 146–147 |
| 110 | 4-Cl | $C_2H_5$ | $C_2H_5$ | 4-$CF_3$ | 118–119 |

-continued

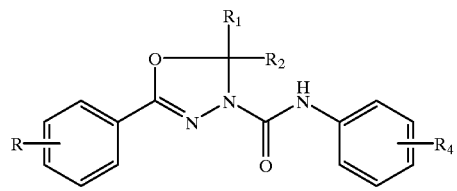

| Example | R | $R_1$ | $R_2$ | $R_4$ | mp ° C. |
|---|---|---|---|---|---|
| 111 | 4-Cl | $C_2H_5$ | $CH_3$ | 4-$OCF_3$ | 119–120 |
| 112 | 4-Cl | $C_2H_5$ | $C_2H_5$ | 4-$OCF_3$ | 84–86 |
| 113 | 4-Cl | $CH_3$ | 3-pyridyl | 4-$CF_3$ | 137–138 |
| 114 | 4-Cl | $CH_3$ | 3-pyridyl | 4-$OCF_3$ | 66–67 |
| 115 | 4-Cl | $CH_3$ | 4-Cl—$C_6H_4$ | 4-$CF_3$ | 219–220 |
| 116 | 4-Cl | $CH_3$ | 4-Cl—$C_6H_4$ | 4-$OCF_3$ | 222–223 |
| 117 | 4-Cl | $CH_3$ | cyclopropyl | 4-$CF_3$ | 170–171 |
| 118 | 4-Cl | $CH_3$ | cyclopropyl | 4-$OCF_3$ | 141–142 |
| 119 | 4-Cl | 1-indanylidene | | 4-$CF_3$ | 76–77 |
| 120 | 4-Cl | $CH_3$ | $CH_2Cl$ | 4-$CF_3$ | 183–184 |
| 121 | 4-Cl | $CH_3$ | $CH_2Cl$ | 4-$OCF_3$ | 166–167 |
| 122 | 4-Cl | $CH_3$ | $CH_2F$ | 4-$CF_3$ | 195–196 |
| 123 | 4-Cl | $CH_3$ | $CH_2F$ | 4-$OCF_3$ | 176–177 |
| 124 | 4-Cl | $CH_2Cl$ | $CH_2Cl$ | 4-$CF_3$ | 197 (dec.) |
| 125 | 4-Cl | $CH_3$ | $CH_2CO_2CH_3$ | 4-$CF_3$ | 145–147 |
| 126 | 4-Cl | $CH_3$ | $CH_2CO_2CH_3$ | 4-$OCF_3$ | 138–139 |
| 127 | 4-Cl | $CH_3$ | $CH_2OC_6H_5$ | 4-$CF_3$ | 128–129 |
| 128 | 4-Cl | $CH_3$ | $CH_2OC_6H_5$ | 4-$OCF_3$ | 100–101 |
| 129 | 4-F | $CH_3$ | $CH_2Cl$ | 4-$CF_3$ | 143–144 |
| 130 | 4-Br | $CH_3$ | $CH_2Cl$ | 4-$CF_3$ | 175–176 |
| 131 | 4-F | $CH_3$ | $CH_2Cl$ | 4-$OCF_3$ | 101–103 |
| 132 | 4-Br | $CH_3$ | $CH_2Cl$ | 4-$OCF_3$ | 155–156 |
| 133 | 4-Cl | $CH_3$ | $CHCl_2$ | 4-$CF_3$ | 175–176 |
| 134 | 4-Cl | $CH_3$ | $CHCl_2$ | 4-$OCF_3$ | 135–136 |
| 135 | 4-Cl | $CH_3$ | $CH_2CF_3$ | 4-$CF_3$ | 131–132 |
| 136 | 4-Cl | $CH_3$ | $CH_2CF_3$ | 4-$OCF_3$ | 106–107 |
| 137 | 4-Cl | $CH_3$ | $CH_2OCH_3$ | 4-$OCF_3$ | 112–113 |
| 138 | 4-Cl | $CH_3$ | $CH_2OCH_3$ | 4-$CF_3$ | 165–166 |
| 139 | 4-Cl | $CH_3$ | $CH_2OC(O)CH_3$ | 4-$CF_3$ | 147–148 |
| 140 | 4-Cl | $CH_3$ | $CH_2OC(O)CH_3$ | 4-$OCF_3$ | 117–118 |
| 141 | 4-Cl | $CH_3$ | 3-thienyl | 4-$OCF_3$ | 223 |
| 142 | 4-Cl | $CH_3$ | 2-thiophene | 4-$CF_3$ | 196 |
| 143 | 4-Cl | $CH_3$ | 2-furyl | 4-$CF_3$ | 172 |
| 144 | 4-Cl | $CH_3$ | 3-thienyl | 4-$CF_3$ | 201 |
| 145 | 4-Cl | $CH_3$ | 2-pyridyl | 4-$CF_3$ | 136 |
| 146 | 4-Cl | $CH_3$ | 2-pyridyl | 4-$OCF_3$ | 135 |
| 147 | 4-Br | $CH_3$ | 2-pyridyl | 4-$CF_3$ | 151–153 |
| 148 | 4-Br | $CH_3$ | 2-pyridyl | 4-$OCF_3$ | 135–136 |
| 149 | 4-Cl | $CH_3$ | $CH_2C_6H_5$ | 4-$OCF_3$ | 125–126 |
| 150 | 4-Cl | $CH_3$ | $CH_2$-4-$OCH_3$—$C_6H_4$ | 4-$CF_3$ | 145 |
| 151 | 4-Cl | $CH_3$ | $CH_2$-4-$OCH_3$—$C_6H_4$ | 4-$OCF_3$ | 124 |
| 152 | 4-I | $CH_3$ | 2-pyridyl | 4-$CF_3$ | 154 |
| 153 | 4-I | $CH_3$ | 2-pyridyl | 4-$OCF_3$ | 151–152 |
| 154 | 4-Cl | $CH_3$ | 4-F—$C_6H_4$ | 4-$CF_3$ | 202 |
| 155 | 4-Cl | $CH_3$ | 4-$OCH_3$—$C_6H_4$ | 4-$CF_3$ | 168–170 |
| 156 | 4-Cl | $CH_3$ | $CH_2C_6H_5$ | 4-$CF_3$ | 130 |
| 157 | 4-Cl | $CH_3$ | 4-F—$C_6H_4$ | 4-$OCF_3$ | 189–190 |
| 158 | 4-Cl | $CH_3$ | 4-Br—$C_6H_4$ | 4-$OCF_3$ | 218–219 |
| 159 | 4-Cl | $CH_3$ | 3,4-di-F—$C_6H_3$ | 4-$OCF_3$ | 110–111 |
| 160 | 4-Cl | $CH_3$ | 3,4-di-Cl—$C_6H_3$ | 4-$CF_3$ | 220 |
| 161 | 4-Cl | $CH_3$ | 4-$CH_3$—$C_6H_4$ | 4-$OCF_3$ | 209 |
| 162 | 4-Cl | $CH_3$ | 3,4-di-F—$C_6H_3$ | 4-$CF_3$ | 172–174 |
| 163 | 4-Cl | $CH_3$ | 4-Br—$C_6H_4$ | 4-$CF_3$ | 206–207 |
| 164 | 4-Cl | $CH_3$ | 4-$CF_3$—$C_6H_4$ | 4-$CF_3$ | 73 |
| 165 | 4-Cl | $CH_3$ | 4-$CF_3$—$C_6H_4$ | 4-$OCF_3$ | 192–193 |

EXAMPLE 166

Preparation of 2-(p-Chlorophenyl)-5-methyl-5-trifluoromethyl-4'-(trifluoromethyl)-$\Delta^2$-1,3,4-oxadiazoline-4-carboxanilide

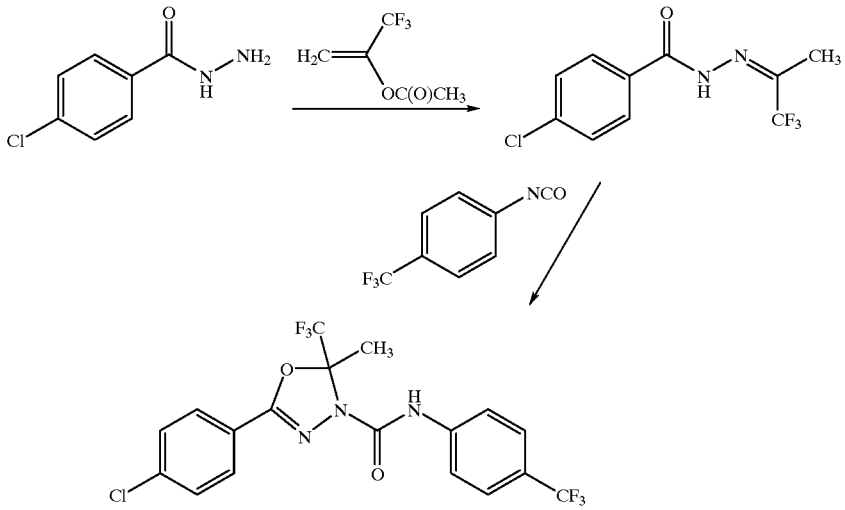

A mixture of p-chlorobenzoyl hydrazine (1.77 g), 1-trifluoromethyl-l-acetoxyethylene (1.78 g) and ethanol (35 mL) is refluxed for 17 hours, cooled to room temperature, and concentrated in vacuo to obtain the corresponding benzoyl hydrazone (0.71 g). A mixture of the hydrazone (0.8 g) and 1,2-dichloroethane (10 mL) is treated with a p-trifluoromethylphenylisocyanate (0.67 g), heated at reflux for 87 hours, and concentrated in vacuo to obtain a colorless solid (1.48 g). Flash chromatography of the solid on silica gel (25% CH$_2$Cl$_2$/hexanes to 50% CH$_2$Cl$_2$/hexanes) gives the title product as a colorless solid (0.16 g, m.p. 157–158° C.).

Using essentially the same procedure as described for Example 166, but using the appropriately substituted hydrazine and isocyanate, the following compounds are obtained.

| Example | R | R$_4$ | mp ° C. |
|---|---|---|---|
| 167 | Cl | OCF$_3$ | 128–129 |
| 168 | Br | CF$_3$ | 156–157 |
| 169 | F | CF$_3$ | 141–142 |

EXAMPLE 170

Preparation of p-chlorobenzoylthiohydrazide

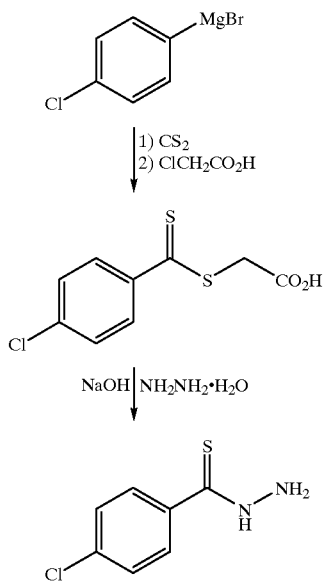

A solution of carbon disulfide (4.5 mL, 75 mmol) and tetrahydrofuran (50 mL) is cooled to 0° C., treated dropwise with a solution p-chlorophenylmagnesium bromide (50 mL of 1M solution) at a rate that maintains the temperature below 10° C., warmed to and stirred at room temperature for 2 hours, concentrated in vacuo and diluted with water. The resultant aqueous mixture is filtered through diatomaceous earth. The filtrate is treated with a solution of chloroacetic acid (5.67 9), sodium hydrogen carbonate (3.82 9) and water (24 mL), stirred for three days at room temperature, acidified to pH 1 with 50% aqueous sulfuric acid and filtered to obtain the thioester (8.98 g). To a cold (0° C.) solution of the thioester (3.5 g), sodium hydroxide (0.58 g) and water (35 mL) is added hydrazine hydrate (1.4 g). During the addition, the color changes from red to yellow and a solid precipitates. The solid is collected, washed with water, and dried to give the title product (1.92 g, m.p. 112–114° C.).

EXAMPLE 171

Preparation of 2-(p-chlorophenyl)-5,5-dimethyl-Δ$^2$-1,3,4-thiadiazoline

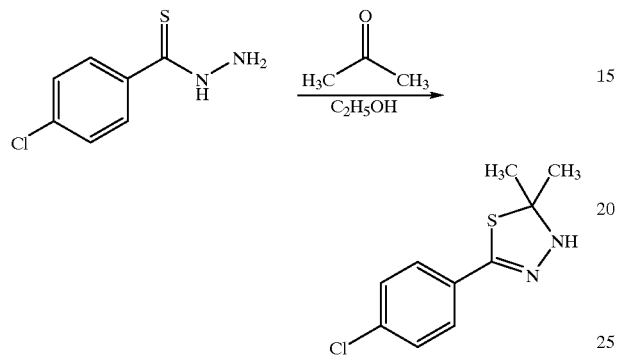

A solution of p-chlorobenzoylthiohydrazine (1.02 g), acetone (1.89 g) and ethanol (5 mL) is stirred at room temperature for 4 days and the solvents are evaporated to obtain a brown solid. Flash chromatography of the brown solid on silica gel (10% ethyl acetate/hexanes) gives the title product as a yellow solid (0.44 g, m.p. 51–53° C.).

EXAMPLE 172

Preparation of 2-(p-Chlorophenyl)-5,5-dimethyl-4'-(trifluoromethyl)-Δ$^2$-1,3,4-thiadiazoline-4-carboxanilide

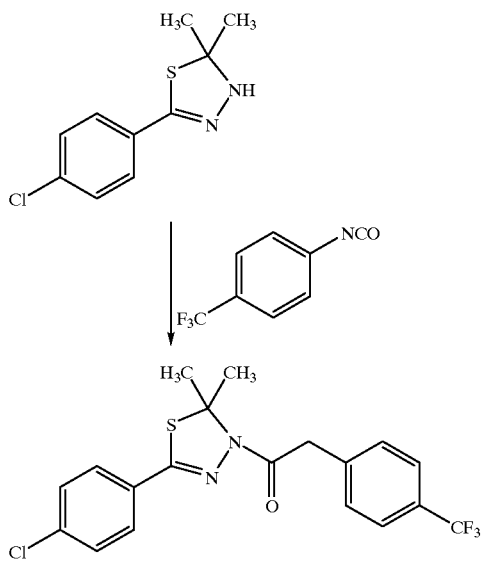

A solution of 2-(p-chlorophenyl)-5,5-dimethyl-Δ$^2$-1,3,4-thiadiazoline (0.33 9) and 1,2-dichloroethane (8 mL) is treated with p-trifluoromethylphenylisocyanate (0.30 g), stirred for 72 hours at room temperature, and concentrated in vacuo to obtain a solid. Flash chromatography of the solid on silica gel (30% methylene chloride/hexanes) gives the title product as a colorless solid (0.61 g, m.p. 129–131° C.).

Using essentially the same procedure as described for Example 172, but using the appropriately substituted isocyanate, the following compound is obtained:

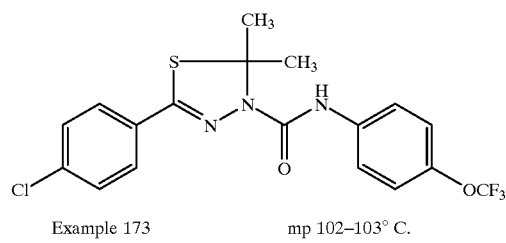

Example 173       mp 102–103° C.

EXAMPLE 174

Preparation of 1-Oxide-2-(p-chlorophenyl)-5,5-dimethyl-4'-(trifluoromethoxy)-Δ$^2$-1,3,4-thiadiazoline-4-carboxanilide

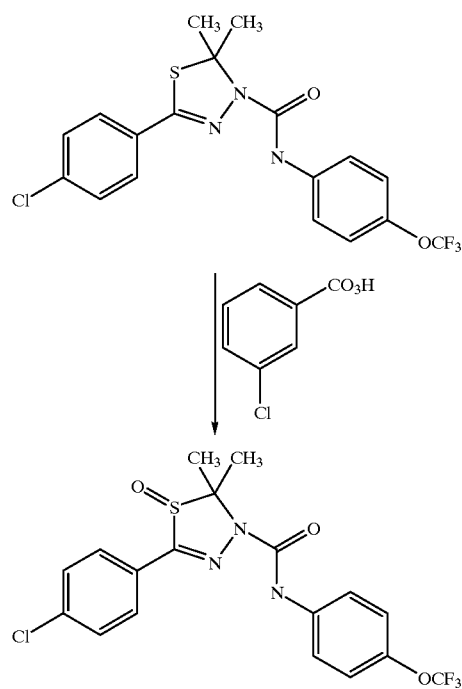

A solution of 2-(p-chlorophenyl)-5,5-dimethyl-4'-(trifluoromethoxy)-Δ$^2$-1,3,4-thiadiazoline-4-carboxanilide (0.50 g) and dichloromethane (15 mL) is stirred at −5° C., treated with 3-chloroperoxybenzoic acid (0.30 g, 70%), stirred for 3.5 hours at room temperature, and diluted with dichloromethane (10 mL). The resultant mixture is washed with 5% sodium carbonate solution, dried over anhydrous magnesium sulfate, concentrated to 10 mL volume, and cooled in a refrigerator overnight. The white precipitate is filtered and dried to give the title product as a colorless solid (0.49 g, m.p. 214–215° C.).

EXAMPLE 175

Preparation of 1,1-Dioxide-2-(p-chlorophenyl)-5,5-dimethyl-4'-(trifluoromethoxy)-$\Delta^2$-1,3,4-thiadiazoline-4-carboxanilide

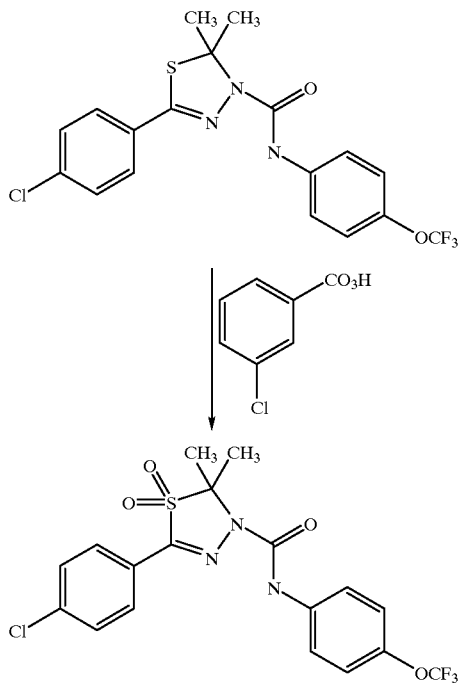

A solution of 2-(p-chlorophenyl)-5,5-dimethyl-4'-(trifluoromethoxy)-$\Delta^2$-1,3,4-thiadiazoline-4-carboxanilide (0.50 g) and dichloromethane (15 mL) is stirred at −5° C., treated with 3-chloroperoxybenzoic acid (1.79 g, 70%), stirred for 18 hours at room temperature, treated with additional 3-chloroperoxybenzoic acid (0.12 9, 70%), stirred for 14 hours at room temperature, washed with 5% sodium carbonate solution, dried over anhydrous magnesium sulfate, and concentrated in vacuo to obtain a solid. Flash chromatography of the solid on silica gel using a 10% ethyl acetate in hexanes solution gives the title product as a colorless solid (0.42 g, m.p. 181° C.).

EXAMPLE 176

Insecticidal and Acaricidal Evaluation of Test Compounds

Test solutions are prepared by dissolving the test compound in a 35% acetone in water mixture to give a concentration of 10,000 ppm. Subsequent dilutions are made with water as needed.

*Spodoptera eridania*, 2nd Instar Larvae, Southern Armyworm (SAW)

A Sieva lima bean leaf expanded to 7–8 cm in length is dipped in the test solution with agitation for 3 seconds and allowed to dry in a hood. The leaf is then placed in a 100×10 mm petri dish containing a damp filter paper on the bottom and ten 2nd instar caterpillars. At 5 days, observations are made of mortality, reduced feeding, or any interference with normal molting.

*Diabrotica virgifera viraifera* Leconte, 2nd Instar Western Corn Rootworm (WCR)

One cc of fine talc is placed in a 30 mL wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed mechanically. Following this, ten 2nd instar rootworms are added to each jar and the jars are loosely capped to allow air exchange for the larvae. The treatments are held for 5 days when mortality counts are made. Missing larvae are presumed dead, since they decompose rapidly and cannot be found. The concentrations of active ingredient used in this test correspond approximately to 50 kg/ha.

*Tetranychus urticae* (OP-resistant strain), 2-Spotted Spider Mite (TSM)

Sieva lima bean plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly-infested plants are dipped in the test solution for 3 seconds with agitation and set in the hood to dry. After 2 days, one leaf is removed and mortality counts are made.

*Aphis gossypii*, Cotton Aphid (CA)

Cotton plants at the cotyledon stage are selected and cut back to one plant per pot. A heavily infested leaf is taken from the main colony and placed on top of each cotyledon. The aphids are allowed to transfer to the host plant overnight. At the time of test treatment, the leaf used to transfer the aphids is removed and discarded. The cotyledons are dipped in the test solution and allowed to dry. After 5 days, mortality counts are made.

*Diabrotica undecimpunctata howardi*, Eggs-southern Corn Rootworm (SCR-Eggs)

Wells containing artificial diet are treated with the test solutions and dried. Southern corn rootworm eggs are then placed in the wells. The wells are covered with vented, adhesive, clear plastic covers. After 7 days, mortality counts are made.

*Heliothis virenscens*, 3rd Instar Tobacco Budworm (TBW)

Cotton cotyledons are dipped in the test solution and allowed to dry in a hood. When dry, each is cut into quarters and ten sections are placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

The tests are rated according to the scale shown below and the data obtained are shown in Table I.

Rating Scale

| | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |

TABLE I

Insecticidal and Acaricidal Evaluations

| Ex. | CA (300[1]) | SAW (300[1]) | TBW (300[1]) | TSM (300[1]) | SCR Eggs (1000[1]) | WCR (50[1]) |
|---|---|---|---|---|---|---|
| 1 | 0 | 9 | 4 | 0 | 9 | 0 |
| 2 | | 9 | 9 | 0 | 9 | |
| 3 | 0 | 9 | 9 | 0 | 9 | 4 |
| 4 | 0 | 4 | | 0 | 0 | 0 |
| 5 | 0 | 9 | 3 | 2 | 9 | 0 |
| 6 | 0 | 9 | 9 | 0 | 9 | 1 |
| 7 | 0 | 9 | 8 | 0 | 9 | 0 |
| 8 | 0 | 0 | | 0 | 0 | 0 |
| 9 | 0 | 9 | 9 | 0 | 9 | 2 |
| 10 | 0 | 9 | 3 | 0 | 9 | 0 |
| 11 | 0 | 0 | | 9 | 0 | 0 |
| 12 | 0 | 9 | 9 | 0 | 9 | 0 |
| 13 | 0 | 7 | 0 | 0 | 0 | 0 |
| 14 | 0 | 9 | 9 | 0 | 9 | 0 |
| 15 | 0 | 0 | | 4 | 0 | 0 |
| 16 | 0 | 8 | 0 | 0 | 9 | 0 |
| 17 | 0 | 9 | 0 | 0 | 0 | 0 |
| 18 | 0 | 0 | | 0 | 0 | 1 |
| 19 | | | | | 0 | |
| 20 | | | | | 0 | |
| 21 | | | | | 0 | |
| 22 | 0 | 1 | | 0 | 0 | 0 |
| 23 | 0 | 8 | 0 | 0 | 0 | 1 |
| 24 | 0 | 2 | | 0 | 0 | 0 |
| 25 | 0 | 2 | | 3 | 0 | 0 |
| 26 | 0 | 0 | | 0 | 0 | 1 |
| 27 | 0 | 9 | 9 | 0 | 9 | 0 |
| 28 | 0 | 9 | 9 | 0 | 9 | 4 |
| 29 | 0 | 9 | 0 | 0 | 9 | 0 |
| 30 | 0 | 9 | 1 | 0 | 9 | 0 |
| 31 | 0 | 9 | 0 | 0 | 9 | 0 |
| 32 | 0 | 9 | 8 | 0 | 9 | 0 |
| 33 | 0 | 9 | 1 | 0 | 9 | 0 |
| 34 | 0 | 9 | 9 | 0 | 9 | 0 |
| 35 | 0 | 9 | 9 | 0 | 9 | 0 |
| 36 | 5 | 9 | 8 | 0 | 9 | 9 |
| 37 | 0 | 9 | 0 | 0 | 9 | 0 |
| 38 | 0 | 9 | 1 | 0 | 8 | 0 |
| 39 | 0 | 9 | 1 | 0 | 9 | 1 |
| 40 | 0 | 9 | 3 | 0 | 9 | 0 |
| 41 | 0 | 9 | 3 | 0 | 9 | 0 |
| 42 | 0 | 1 | | 0 | 9 | 0 |
| 43 | 0 | 9 | 9 | 0 | 9 | 0 |
| 44 | 0 | 9 | 0 | 0 | 9 | 0 |
| 45 | 0 | 8 | 0 | 0 | 0 | 0 |
| 46 | 0 | 8 | 0 | 0 | 0 | 0 |
| 47 | 0 | 9 | 5 | 0 | 0 | 0 |
| 48 | 0 | 9 | 6 | 0 | 9 | 0 |
| 49 | 0 | 9 | 1 | 0 | 9 | 7 |
| 50 | 0 | 9 | 0 | 0 | 0 | 0 |
| 51 | 0 | 9 | 5 | 0 | 0 | 0 |
| 52 | 0 | 9 | 0 | 0 | 0 | 0 |
| 53 | 0 | 9 | 0 | 0 | 9 | 4 |
| 54 | 0 | | | 0 | 0 | 4 |
| 55 | 0 | | | 0 | 8 | 0 |
| 56 | 0 | | | 0 | 8 | 0 |
| 57 | 8 | 0 | | 0 | 7 | 0 |
| 58 | 0 | 8 | | 0 | 0 | 0 |
| 59 | 0 | 9 | 9 | 0 | 9 | 0 |
| 60 | 0 | 9 | 9 | 0 | 9 | 0 |
| 61 | 0 | 9 | 0 | 0 | 9 | 0 |
| 62 | 0 | 9 | 1 | 0 | 0 | 0 |
| 63 | 0 | 9 | 0 | 0 | 9 | 0 |
| 64 | 0 | 9 | 9 | 0 | 9 | 0 |
| 65 | 0 | 9 | 7 | 0 | 9 | 0 |
| 66 | 0 | 4 | | 0 | 0 | 0 |
| 67 | 0 | 9 | 9 | 0 | 9 | 0 |
| 68 | 0 | 8 | 1 | 0 | 8 | 9 |
| 69 | 0 | 9 | 9 | 0 | 9 | 2 |
| 70 | 0 | 3 | | 0 | 0 | 1 |
| 71 | 0 | 1 | | 0 | 0 | 3 |
| 72 | 0 | 1 | | 0 | 0 | 2 |
| 73 | | 6 | | 0 | 9 | 2 |
| 74 | 0 | 9 | 6 | 0 | 7 | 1 |
| 75 | 0 | 1 | | 0 | 7 | 9 |
| 76 | 0 | 0 | | 0 | 0 | 4 |
| 77 | 0 | 9 | 0 | 0 | 8 | 0 |
| 78 | 0 | 9 | 0 | 0 | 8 | 0 |
| 79 | 0 | 9 | 0 | 0 | 9 | 1 |
| 80 | 0 | 3 | | 0 | 0 | 9 |
| 81 | 0 | 1 | | 0 | 0 | 0 |
| 82 | 0 | 6 | | 0 | 0 | 2 |
| 83 | 0 | 3 | | 0 | 0 | 0 |
| 84 | 0 | 0 | | 0 | 0 | 0 |
| 85 | 0 | 0 | | 0 | 0 | 3 |
| 86 | 0 | 9 | 9 | 0 | 0 | 4 |
| 87 | 0 | 9 | 8 | 0 | 0 | 9 |
| 88 | 0 | 9 | 0 | 0 | 0 | 0 |
| 89 | 0 | 9 | 1 | 0 | 0 | 0 |
| 90 | 0 | 8 | 0 | 0 | 0 | 0 |
| 91 | 0 | 9 | 7 | 0 | 0 | 0 |
| 92 | 0 | 9 | 0 | 0 | 0 | 0 |
| 93 | 0 | 9 | 0 | 0 | 0 | 0 |
| 94 | 0 | 9 | 7 | 0 | 0 | 0 |
| 95 | 0 | 9 | 9 | 0 | 9 | 0 |
| 96 | 0 | 0 | | 0 | 0 | 0 |
| 97 | 0 | 9 | 3 | 0 | 9 | 0 |
| 98 | 0 | 9 | 3 | 0 | 9 | 1 |
| 99 | 0 | 9 | 0 | 0 | 0 | 0 |
| 100 | 0 | 0 | | 0 | 0 | 0 |
| 101 | 0 | 9 | 8 | 0 | 9 | 0 |
| 102 | 0 | 9 | 6 | 0 | 7 | 0 |
| 103 | 0 | 9 | 9 | 0 | 8 | 0 |
| 104 | 0 | 9 | 2 | 0 | 8 | 0 |
| 105 | 0 | 9 | 3 | 0 | 0 | 0 |
| 106 | 0 | 9 | 1 | 0 | 9 | 1 |
| 107 | 0 | 9 | 2 | 0 | 9 | 0 |
| 108 | 0 | 0 | | 0 | 0 | 4 |
| 109 | 0 | 9 | 8 | 0 | 9 | 0 |
| 110 | 0 | 9 | 7 | 0 | 9 | 0 |
| 111 | 0 | 9 | 9 | 4 | 9 | 9 |
| 112 | 0 | 9 | 9 | 0 | 9 | 3 |
| 113 | 0 | 9 | 4 | 0 | 9 | 4 |
| 114 | 0 | 9 | 2 | 0 | 9 | 2 |
| 115 | 0 | 9 | 9 | 0 | 9 | 3 |
| 116 | 0 | 9 | 9 | 0 | 8 | 3 |
| 117 | 0 | 9 | 7 | 0 | 8 | 0 |
| 118 | 0 | 7 | 0 | 0 | 8 | 0 |
| 119 | 0 | 8 | 9 | 0 | 0 | 0 |
| 120 | 0 | 9 | 9 | 0 | 9 | 0 |
| 121 | 0 | 9 | 9 | 0 | 9 | 3 |
| 122 | 0 | 9 | 8 | 0 | 0 | 0 |
| 123 | 0 | 9 | 9 | 0 | 0 | 0 |
| 124 | 0 | 5 | | 0 | 0 | 0 |
| 125 | 0 | 9 | 7 | 0 | 8 | 0 |
| 126 | 0 | 9 | 0 | 0 | 9 | 0 |
| 127 | 0 | 9 | 6 | 0 | 8 | 3 |
| 128 | 0 | 9 | 6 | 0 | 9 | 3 |
| 129 | 0 | 9 | 9 | 0 | 0 | 2 |
| 130 | 0 | 9 | 9 | 0 | 0 | 0 |
| 131 | 0 | 9 | 9 | 0 | 0 | 0 |
| 132 | 0 | 9 | 9 | 0 | 0 | 0 |
| 133 | 0 | 9 | 8 | 0 | 0 | 0 |

TABLE I-continued

Insecticidal and Acaricidal Evaluations

| Ex. | CA (300[1]) | SAW (300[1]) | TBW (300[1]) | TSM (300[1]) | SCR Eggs (1000[1]) | WCR (50[1]) |
|---|---|---|---|---|---|---|
| 134 | 7 | 9 | 6 | 2 | | 1 |
| 135 | 0 | 9 | | 0 | | 1 |
| 136 | 0 | 9 | | 0 | | 2 |
| 137 | 0 | 9 | | 3 | | 0 |
| 138 | 0 | 6 | | 0 | | 9 |
| 139 | 0 | 8 | | 0 | | 2 |
| 140 | 0 | 9 | | 0 | | 3 |
| 141 | 0 | 8 | 0 | 0 | 9 | 0 |
| 142 | 0 | 2 | | 0 | 0 | 1 |
| 143 | 0 | 0 | | 0 | 0 | 0 |
| 144 | 0 | 2 | | 0 | 9 | 2 |
| 145 | 0 | 9 | 0 | 0 | 0 | 6 |
| 146 | 0 | 9 | 8 | 0 | 9 | 0 |
| 147 | 0 | 9 | | 0 | 0 | 6 |
| 148 | 0 | 6 | | 0 | 0 | 7 |
| 149 | 0 | 9 | | 0 | 9 | 0 |
| 150 | 0 | 0 | | 0 | 0 | 0 |
| 151 | 0 | 0 | | 0 | 9 | 0 |
| 152 | 0 | 4 | 0 | 0 | 9 | 0 |
| 153 | 0 | 0 | | 0 | 0 | 0 |
| 154 | 0 | 9 | 4 | 0 | 8 | 0 |
| 155 | 0 | 9 | 0 | 0 | 9 | 0 |
| 156 | 0 | 0 | | 0 | 9 | 0 |
| 157 | 0 | 9 | 9 | 0 | 9 | 4 |
| 158 | 0 | 8 | 0 | 0 | 9 | 0 |
| 159 | 0 | 9 | 9 | 0 | 9 | 0 |
| 160 | 0 | 4 | | 0 | 9 | 3 |
| 161 | 0 | 9 | 7 | 0 | 0 | 0 |
| 162 | 0 | 9 | 9 | 0 | 8 | 0 |
| 163 | 0 | 6 | | 0 | 8 | 0 |
| 164 | 0 | 9 | 7 | 0 | | 3 |
| 165 | 0 | 9 | | 0 | | 8 |
| 166 | 0 | 9 | 9 | 0 | 9 | 0 |
| 167 | 0 | 9 | 9 | 0 | 7 | 4 |
| 168 | 0 | 9 | 9 | 0 | 9 | 0 |
| 169 | 0 | 9 | 9 | 0 | 9 | 0 |
| 172 | 0 | 9 | 9 | 0 | | 0 |
| 173 | 0 | 9 | 9 | 0 | | 0 |

[1]rates in ppm

What is claimed is:

1. A method for the control of insect or acarid pests which comprises contacting said pests or their food supply, habitat or breeding grounds with a pesticidally effective amount of a compound having the structural formula

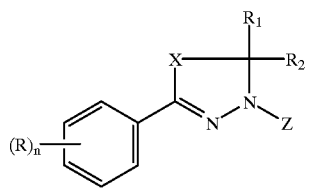

wherein

X is O or $S(O)_m$;

Z is

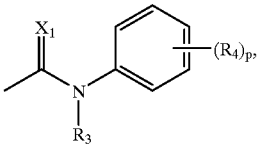

$C(X_1)R_5$, $C_1$–$C_6$alkyl, $C_1$–$C_6$haloalkyl,
benzyl optionally substituted on the phenyl ring with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, or
phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups,
provided that when X is O, Z is

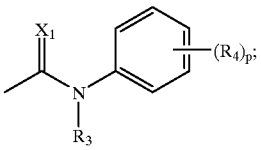

n and p are each independently 0, 1, 2 or 3;
$X_1$ is O or S;
R and $R_4$ are each independently halogen, $C_1$–$C_6$alkyl, $C_1$–$C_6$haloalkyl, $OR_6$, $S(O)_qR_7$, nitro, cyano, $NR_8R_9$, $CO_2R_{10}$, $C(O)R_{11}$ or
phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, or
two adjacent R groups or $R_4$ groups may be taken together to form a ring wherein RR or $R_4R_4$ is represented by: —$OCH_2O$—, —$OCF_2O$— or —CH=CH—CH=CH—;
$R_6$ and $R_7$ are each independently hydrogen, $C_1$–$C_6$alkyl, $C_1$–$C_6$haloalkyl or
phenyl optionally substituted with any combination of from one to three halogen, $C_1$–$C_6$alkyl, $C_1$–$C_6$haloalkyl, $C_1$–$C_6$alkoxy, $C_1$–$C_4$haloalkoxy, $C_1$–$C_6$alkylthio or $C_1$–$C_6$haloalkylthio groups;
$R_8$, $R_9$, $R_{13}$ and $R_{14}$ are each independently hydrogen, $C_1$–$C_6$alkyl, $C_1$–$C_6$alkylcarbonyl or
phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups;
$R_{10}$ and $R_{11}$ are each independently hydrogen, $C_1$–$C_6$alkyl or $C_1$–$C_6$haloalkyl;
$R_1$ and $R_2$ are each independently hydrogen, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_2$–$C_6$alkoxyalkyl, $(CH_2)_vC(O)R_{12}$,
$C_1$–$C_6$alkyl optionally substituted with one phenoxy or phenyl group wherein the phenyl ring of each group is independently, optionally substituted with from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, phenyl optionally substituted with from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, or a 5- or 6-membered heteroaromatic ring optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, and when $R_1$ and $R_2$ are taken together with the atom to which they are attached they may form a $C_3$–$C_6$cycloalkyl ring wherein $R_1R_2$ is represented by: —$(CH_2)_t$— where t is 2, 3, 4 or 5;

m, q and v are each independently 0, 1 or 2;

$R_{12}$ is hydrogen, $C_1$–$C_6$alkyl, $C_1$–$C_6$haloalkyl, $C_1$–$C_6$alkoxy, $C_1$–$C_6$haloalkoxy, $C_1$–$C_6$alkylthio, $C_1$–$C_6$haloalkylthio or $NR_{13}R_{14}$;

$R_3$ is hydrogen, $C_1$–$C_6$alkyl, $C_1$–$C_6$haloalkyl or $C(O)R_{15}$;

$R_{15}$ is $C_1$–$C_6$alkyl, $C_1$–$C_6$haloalkyl, $C_1$–$C_6$alkoxy or $C_1$–$C_6$haloalkoxy; and $R_5$ is $C_1$–$C_6$alkyl, phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, or benzyl optionally substituted on the phenyl ring with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups; and the optical isomers thereof and the agriculturally acceptable salts thereof.

2. The method according to claim 1 wherein the compound has the structural formula

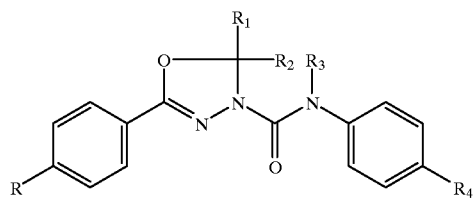

wherein

R is halogen, $C_1$–$C_4$haloalkyl, $C_1$–$C_4$haloalkoxy or phenoxy optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

$R_4$ is $C_1$–$C_4$haloalkyl, $C_1$–$C_4$haloalkoxy or $C_1$–$C_4$haloalkylthio;

$R_1$ is $C_1$–$C_4$alkyl;

$R_2$ is $C_1$–$C_4$alkyl, $C_1$–$C_4$haloalkyl, $(CH_2)_vC(O)R_{12}$ or 2-pyridyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

v is 0 or 1;

$R_{12}$ is $C_1$–$C_4$alkoxy or $C_1$–$C_4$haloalkoxy;

$R_3$ is hydrogen or $C(O)R_{15}$; and $R_{15}$ is $C_1$–$C_4$alkoxy.

3. The method according to claim 2 wherein

R is F, Br, Cl or phenoxy;

$R_4$ is $CF_3$, $OCF_3$ or $SCF_3$;

$R_1$ is $CH_3$;

$R_2$ is $CH_3$, $CH_2Cl$, $CH_2CF_3$, $CF_3$, $CH_2CO_2CH_3$ or 2-pyridyl; and $R_3$ is hydrogen or $CO_2CH_3$.

4. The method according to claim 1 wherein the compound is selected from the group consisting of 2-(p-chlorophenyl)-5,5-dimethyl-4'-(trifluoromethoxy)-$\Delta^2$-1,3,4-oxadiazoline-4-carboxanilide;

2-(p-chlorophenyl)-5,5-dimethyl-4'-(trifluoromethyl)-$\Delta^2$-1,3,4-oxadiazoline-4-carboxanilide;

2-(p-bromophenyl)-5,5-dimethyl-4'-(trifluoromethyl)-$\Delta^2$-1,3,4-oxadiazoline-4-carboxanilide;

2-(p-fluorophenyl)-5,5-dimethyl-4'-(trifluoromethyl)-$\Delta^2$-1,3,4-oxadiazoline-4-carboxanilide;

5,5-dimethyl-2-(p-phenoxyphenyl)-4'-[(trifluoromethyl)thio]-$\Delta^2$-1,3,4-oxadiazoline-4-carboxanilide;

2-(p-chlorophenyl)-5-methyl-4'-(trifluoromethoxy)-5-(trifluoromethyl)-$\Delta^2$-1,3,4-oxadiazoline-4-carboxanilide;

5-(chloromethyl)-2-(p-chlorophenyl)-5-methyl-4'-(trifluoromethyl)-$\Delta^2$-1,3,4-oxadiazoline-4-carboxanilide;

4,5-bis(trifluoromethyl)-2-(p-fluorophenyl)-5-methyl-$\Delta^2$-1,3,4-oxadiazoline-4-carboxanilide;

5-(chloromethyl)-2-(p-fluorophenyl)-5-methyl-4'-(trifluoromethyl)-$\Delta^2$-1,3,4-oxadiazoline-4-carboxanilide;

5-(chloromethyl)-2-(p-fluorophenyl)-5-methyl-4'-(trifluoromethoxy)-$\Delta^2$-1,3,4-oxadiazoline-4-carboxanilide;

2-(p-bromophenyl)-5-(chloromethyl)-5-methyl-4'-(trifluoromethoxy)-$\Delta^2$-1,3,4-oxadiazoline-4-carboxanilide;

2-(p-chlorophenyl)-5-methyl-5-(2,2,2-trifluoroethyl)-4'-(trifluoromethyl)-$\Delta^2$-1,3,4-oxadiazoline-4-carboxanilide;

2-(p-chlorophenyl)-5-methyl-5-(2,2,2-trifluoroethyl)-4'-(trifluoromethoxy)-$\Delta^2$-1,3,4-oxadiazoline-4-carboxanilide;

2-(p-chlorophenyl)-5-methyl-5-(2-pyridyl)-4'-(trifluoromethyl)-$\Delta^2$-1,3,4-oxadiazoline-4-carboxanilide;

2-(p-chlorophenyl)-5-methyl-5-(2-pyridyl)-4'-(trifluoromethoxy)-$\Delta^2$-1,3,4-oxadiazoline-4-carboxanilide;

methyl N-{[2-(p-chlorophenyl)-5,5-dimethyl-$\Delta^2$-1,3,4-oxadiazolin-4-yl]carbonyl}-p-(trifluoromethoxy)-carbanilate;

methyl N-{[2-(p-chlorophenyl)-5,5-dimethyl-$\Delta^2$-1,3,4-oxadiazolin-4-yl]carbonyl}-p-(trifluoromethyl)-carbanilate; and methyl 2-(p-chlorophenyl)-5-methyl-4-{[p-(trifluoromethoxy)phenyl]carbamoyl}-$\Delta^2$-1,3,4-oxadiazoline-5-acetate.

5. A method for the protection of growing plants from attack or infestation by insect or acarid pests which comprises applying to the foliage of the plants, or to the soil or water in which they are growing, a pesticidally effective amount of a compound having the structural formula

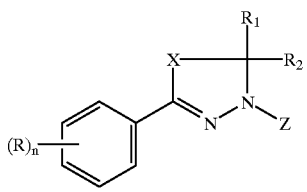

wherein n, R, $R_1$, $R_2$, X and Z are as described in claim 1.

6. The method according to claim 5 wherein the compound has the structural formula

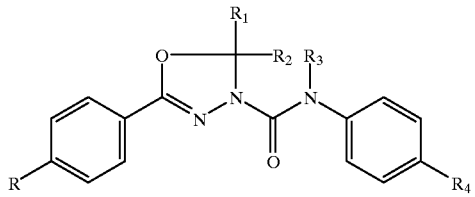

wherein

R is halogen, $C_1$–$C_4$haloalkyl, $C_1$–$C_4$haloalkoxy or phenoxy optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

$R_4$ is $C_1$–$C_4$haloalkyl, $C_1$–$C_4$haloalkoxy or $C_1$–$C_4$haloalkylthio;

$R_1$ is $C_1$–$C_4$alkyl;

$R_2$ is $C_1$–$C_4$alkyl, $C_1$–$C_4$haloalkyl, $(CH_2)_vC(O)R_{12}$ or 2-pyridyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

v is 0 or 1;

$R_{12}$ is $C_1$–$C_4$alkoxy or $C_1$–$C_4$haloalkoxy;

$R_3$ is hydrogen or $C(O)R_{15}$; and $R_{15}$ is $C_1$–$C_4$alkoxy.

7. The method according to claim 6 wherein

R is F, Br, Cl or phenoxy;

$R_4$ is $CF_3$, $OCF_3$ or $SCF_3$;

$R_1$ is $CH_3$;

$R_2$ is $CH_3$, $CH_2Cl$, $CH_2CF_3$, $CF_3$, $CH_2CO_2CH_3$ or 2-pyridyl; and $R_3$ is hydrogen or $CO_2CH_3$.

8. The method according to claim 5 wherein the compound is selected from the group consisting of 2-(p-chlorophenyl)-5,5-dimethyl-4'-(trifluoromethoxy)-$\Delta^2$-1,3,4-oxadiazoline-4-carboxanilide;

2-(p-chlorophenyl)-5,5-dimethyl-4'-(trifluoromethyl)-$\Delta^2$-1,3,4-oxadiazoline-4-carboxanilide;

2-(p-bromophenyl)-5,5-dimethyl-4'-(trifluoromethyl)-$\Delta^2$-1,3,4-oxadiazoline-4-carboxanilide;

2-(p-fluorophenyl)-5,5-dimethyl-4'-(trifluoromethyl)-$\Delta^2$-1,3,4-oxadiazoline-4-carboxanilide;

5,5-dimethyl-2-(p-phenoxyphenyl)-4'-[(trifluoromethyl)thio]-$\Delta^2$-1,3,4-oxadiazoline-4-carboxanilide;

2-(p-chlorophenyl)-5-methyl-4'-(trifluoromethoxy)-5-(trifluoromethyl)-$\Delta^2$-1,3,4-oxadiazoline-4-carboxanilide;

5-(chloromethyl)-2-(p-chlorophenyl)-5-methyl-4'-(trifluoromethyl)-$\Delta^2$-1,3,4-oxadiazoline-4-carboxanilide;

4,5-bis(trifluoromethyl)-2-(p-fluorophenyl)-5-methyl-$\Delta^2$-1,3,4-oxadiazoline-4-carboxanilide;

5-(chloromethyl)-2-(p-fluorophenyl)-5-methyl-4'-(trifluoromethyl)-$\Delta^2$-1,3,4-oxadiazoline-4-carboxanilide;

5-(chloromethyl)-2-(p-fluorophenyl)-5-methyl-4'-(trifluoromethoxy)-$\Delta^2$-1,3,4-oxadiazoline-4-carboxanilide;

2-(p-bromophenyl)-5-(chloromethyl)-5-methyl-4'-(trifluoromethoxy)-$\Delta^2$-1,3,4-oxadiazoline-4-carboxanilide;

2-(p-chlorophenyl)-5-methyl-5-(2,2,2-trifluoroethyl)-4'-(trifluoromethyl)-$\Delta^2$-1,3,4-oxadiazoline-4-carboxanilide;

2-(p-chlorophenyl)-5-methyl-5-(2,2,2-trifluoroethyl)-4'-(trifluoromethoxy)-$\Delta^2$-1,3,4-oxadiazoline-4-carboxanilide;

2-(p-chlorophenyl)-5-methyl-5-(2-pyridyl)-4'-(trifluoromethyl)-$\Delta^2$-1,3,4-oxadiazoline-4-carboxanilide;

2-(p-chlorophenyl)-5-methyl-5-(2-pyridyl)-4'-(trifluoromethoxy)-$\Delta^2$-1,3,4-oxadiazoline-4-carboxanilide;

methyl N-{[2-(p-chlorophenyl)-5,5-dimethyl-$\Delta^2$-1,3,4-oxadiazolin-4-yl]carbonyl}-p-(trifluoromethoxy)-carbanilate;

methyl N-{[2-(p-chlorophenyl)-5,5-dimethyl-$\Delta^2$-1,3,4-oxadiazolin-4-yl]carbonyl}-p-(trifluoromethyl)-carbanilate; and methyl 2-(p-chlorophenyl)-5-methyl-4-{[p-(trifluoromethoxy)phenyl]carbamoyl}-$\Delta^2$-1,3,4-oxadiazoline-5-acetate.

9. The method according to claim 5 wherein the compound is applied to the plants, or to the soil or water in which they are growing, at a rate of about 0.1 kg/ha to 4.0 kg/ha.

10. A compound having the structural formula

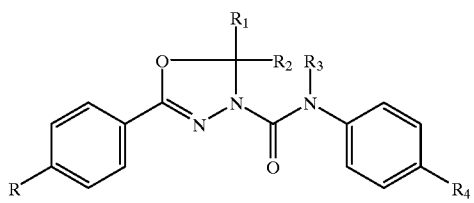

wherein

R is halogen, $C_1$–$C_4$haloalkyl, $C_1$–$C_4$haloalkoxy or phenoxy optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

$R_4$ is $C_1$–$C_4$haloalkyl, $C_1$–$C_4$haloalkoxy or $C_1$–$C_4$haloalkylthio;

$R_1$ is $C_1$–$C_4$alkyl;

$R_2$ is $C_1$–$C_4$alkyl, $C_1$–$C_4$haloalkyl, $(CH_2)_vC(O)R_{12}$ or 2-pyridyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

v is 0 or 1;

$R_{12}$ is $C_1$–$C_4$alkoxy or $C_1$–$C_4$haloalkoxy;

$R_3$ is hydrogen or $C(O)R_{15}$; and $R_{15}$ is $C_1$–$C_4$alkoxy.

11. The compound according to claim 10 wherein

R is F, Br, Cl or phenoxy;

$R_4$ is $CF_3$, $OCF_3$ or $SCF_3$;

$R_1$ is $CH_3$;

$R_2$ is $CH_3$, $CH_2Cl$, $CH_2CF_3$, $CF_3$, $CH_2CO_2CH_3$ or 2-pyridyl; and $R_3$ is hydrogen or $CO_2CH_3$.

12. A compound selected from the group consisting of
2-(p-chlorophenyl)-5,5-dimethyl-4'-(trifluoromethoxy)-$\Delta^2$-1,3,4-oxadiazoline-4-carboxanilide;

2-(p-chlorophenyl)-5,5-dimethyl-4'-(trifluoromethyl)-$\Delta^2$-1,3,4-oxadiazoline-4-carboxanilide;

2-(p-bromophenyl)-5,5-dimethyl-4'-(trifluoromethyl)-$\Delta^2$-1,3,4-oxadiazoline-4-carboxanilide;

2-(p-fluorophenyl)-5,5-dimethyl-4'-(trifluoromethyl)-$\Delta^2$-1,3,4-oxadiazoline-4-carboxanilide;

5,5-dimethyl-2-(p-phenoxyphenyl)-4'-[(trifluoromethyl)thio]-$\Delta^2$-1,3,4-oxadiazoline-4-carboxanilide;

2-(p-chlorophenyl)-5-methyl-4'-(trifluoromethoxy)-5-(trifluoromethyl)-$\Delta^2$-1,3,4-oxadiazoline-4-carboxanilide;

5-(chloromethyl)-2-(p-chlorophenyl)-5-methyl-4'-(trifluoromethyl)-$\Delta^2$-1,3,4-oxadiazoline-4-carboxanilide;

4,5-bis(trifluoromethyl)-2-(p-fluorophenyl)-5-methyl-$\Delta^2$-1,3,4-oxadiazoline-4-carboxanilide;

5-(chloromethyl)-2-(p-fluorophenyl)-5-methyl-4'-(trifluoromethyl)-$\Delta^2$-1,3,4-oxadiazoline-4-carboxanilide;

5-(chloromethyl)-2-(p-fluorophenyl)-5-methyl-4'-(trifluoromethoxy)-$\Delta^2$-1,3,4-oxadiazoline-4-carboxanilide;

2-(p-bromophenyl)-5-(chloromethyl)-5-methyl-4'-(trifluoromethoxy)-$\Delta^2$-1,3,4-oxadiazoline-4-carboxanilide;

2-(p-chlorophenyl)-5-methyl-5-(2,2,2-trifluoroethyl)-4'-(trifluoromethyl)-$\Delta^2$-1,3,4-oxadiazoline-4-carboxanilide;

2-(p-chlorophenyl)-5-methyl-5-(2,2,2-trifluoroethyl)-4'-(trifluoromethoxy)-$\Delta^2$-1,3,4-oxadiazoline-4-carboxanilide;

2-(p-chlorophenyl)-5-methyl-5-(2-pyridyl)-4'-(trifluoromethyl)-$\Delta^2$-1,3,4-oxadiazoline-4-carboxanilide;

2-(p-chlorophenyl)-5-methyl-5-(2-pyridyl)-4'-(trifluoromethoxy)-$\Delta^2$-1,3,4-oxadiazoline-4-carboxanilide;

methyl N-{[2-(p-chlorophenyl)-5,5-dimethyl-$\Delta^2$-1,3,4-oxadiazolin-4-yl]carbonyl}-p-(trifluoromethoxy)-carbanilate;

methyl N-{[2-(p-chlorophenyl)-5,5-dimethyl-$\Delta^2$-1,3,4-oxadiazolin-4-yl]carbonyl}-p-(trifluoromethyl)-carbanilate; and methyl 2-(p-chlorophenyl)-5-methyl-4-{[p-(trifluoromethoxy)phenyl]carbamoyl}-$\Delta^2$-1,3,4-oxadiazoline-5-acetate.

13. A composition for the control of insect or acarid pests which comprises an agronomically acceptable carrier and a pesticidally effective amount of a compound having the structural formula

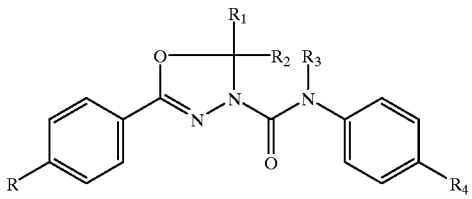

wherein

R is halogen, $C_1$–$C_4$haloalkyl, $C_1$–$C_4$haloalkoxy or phenoxy optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

$R_4$ is $C_1$–$C_4$haloalkyl, $C_1$–$C_4$haloalkoxy or $C_1$–$C_4$haloalkylthio;

$R_1$ is $C_1$–$C_4$alkyl;

$R_2$ is $C_1$–$C_4$alkyl, $C_1$–$C_4$haloalkyl, $(CH_2)_vC(O)R_{12}$ or 2-pyridyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

v is 0 or 1;

$R_{12}$ is $C_1$–$C_4$alkoxy or $C_1$–$C_4$haloalkoxy;

$R_3$ is hydrogen, $C_1$–$C_6$alkyl or $C(O)R_{15}$; and $R_{15}$ is $C_1$–$C_4$alkoxy.

14. The composition according to claim 13 wherein

R is F, Br, Cl or phenoxy;

$R_4$ is $CF_3$, $OCF_3$ or $SCF_3$;

$R_1$ is $CH_3$;

$R_2$ is $CH_3$, $CH_2Cl$, $CH_2CF_3$, $CF_3$, $CH_2CO_2CH_3$ or 2-pyridyl; and $R_3$ is hydrogen or $CO_2CH_3$.

15. The composition according to claim 14 wherein the compound is selected from the group consisting of 2-(p-chlorophenyl)-5,5-dimethyl-4'-(trifluoromethoxy)-$\Delta^2$-1,3,4-oxadiazoline-4-carboxanilide;

2-(p-chlorophenyl)-5,5-dimethyl-4'-(trifluoromethyl)-$\Delta^2$-1,3,4-oxadiazoline-4-carboxanilide;

2-(p-bromophenyl)-5,5-dimethyl-4'-(trifluoromethyl)-$\Delta^2$-1,3,4-oxadiazoline-4-carboxanilide;

2-(p-fluorophenyl)-5,5-dimethyl-4'-(trifluoromethyl)-$\Delta^2$-1,3,4-oxadiazoline-4-carboxanilide;

5,5-dimethyl-2-(p-phenoxyphenyl)-4'-[(trifluoromethyl)thio]-$\Delta^2$-1,3,4-oxadiazoline-4-carboxanilide;

2-(p-chlorophenyl)-5-methyl-4'-(trifluoromethoxy)-5-(trifluoromethyl)-$\Delta^2$-1,3,4-oxadiazoline-4-carboxanilide;

5-(chloromethyl)-2-(p-chlorophenyl)-5-methyl-4'-(trifluoromethyl)-$\Delta^2$-1,3,4-oxadiazoline-4-carboxanilide;

4,5-bis(trifluoromethyl)-2-(p-fluorophenyl)-5-methyl-$\Delta^2$-1,3,4-oxadiazoline-4-carboxanilide;

5-(chloromethyl)-2-(p-fluorophenyl)-5-methyl-4'-(trifluoromethyl)-$\Delta^2$-1,3,4-oxadiazoline-4-carboxanilide;

5-(chloromethyl)-2-(p-fluorophenyl)-5-methyl-4'-(trifluoromethoxy)-$\Delta^2$-1,3,4-oxadiazoline-4-carboxanilide;

2-(p-bromophenyl)-5-(chloromethyl)-5-methyl-4'-(trifluoromethoxy)-$\Delta^2$-1,3,4-oxadiazoline-4-carboxanilide;

2-(p-chlorophenyl)-5-methyl-5-(2,2,2-trifluoroethyl)-4'-(trifluoromethyl)-Δ²-1,3,4-oxadiazoline-4-carboxanilide;

2-(p-chlorophenyl)-5-methyl-5-(2,2,2-trifluoroethyl)-4'-(trifluoromethoxy)-Δ²-1,3,4-oxadiazoline-4-carboxanilide;

2-(p-chlorophenyl)-5-methyl-5-(2-pyridyl)-4'-(trifluoromethyl)-Δ²-1,3,4-oxadiazoline-4-carboxanilide;

2-(p-chlorophenyl)-5-methyl-5-(2-pyridyl)-4'-(trifluoromethoxy)-Δ²-1,3,4-oxadiazoline-4-carboxanilide;

methyl N-{[2-(p-chlorophenyl)-5,5-dimethyl-Δ²-1,3,4-oxadiazolin-4-yl]carbonyl}-p-(trifluoromethoxy)-carbanilate;

methyl N-{[2-(p-chlorophenyl)-5,5-dimethyl-Δ²-1,3,4-oxadiazolin-4-yl]carbonyl}-p-(trifluoromethyl)-carbanilate; and methyl 2-(p-chlorophenyl)-5-methyl-4-{[p-(trifluoromethoxy)phenyl]carbamoyl}-Δ²-1,3,4-oxadiazoline-5-acetate.

16. A composition for the control of insect or acarid pests which comprises an agronomically acceptable carrier, and an insecticidal or acaricidal effective amount of a compound having the structural formula

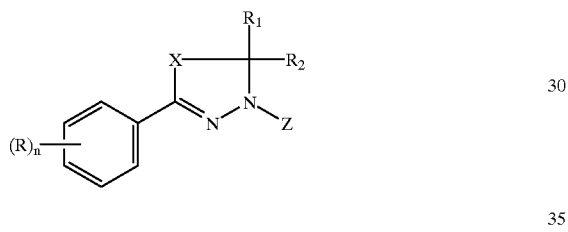

wherein

X is O or $S(O)_m$;

Z is

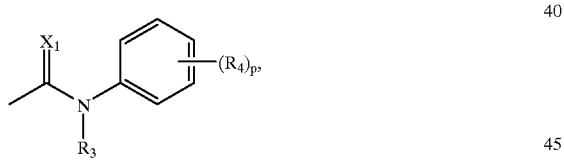

$C(X_1)R_5$, $C_1$–$C_6$alkyl, $C_1$–$C_6$haloalkyl, or
benzyl optionally substituted on the phenyl ring with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups;

$X_1$ is O or S;

R and $R_4$ are each independently halogen, $C_1$–$C_6$alkyl, $C_1$–$C_6$haloalkyl, $OR_6$, $S(O)_qR_7$, nitro, cyano, $NR_8R_9$, $CO_2R_{10}$, $C(O)R_{11}$ or
phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, or
two adjacent R groups or $R_4$ groups may be taken together to form a ring wherein RR or $R_4R_4$ is represented by: —OCH$_2$O—, —OCF$_2$O— or —CH=CH—CH=CH—;

$R_6$ and $R_7$ are each independently hydrogen, $C_1$–$C_6$alkyl, $C_1$–$C_6$haloalkyl or
phenyl optionally substituted with any combination of from one to three halogen, $C_1$–$C_6$alkyl, $C_1$–$C_6$haloalkyl, $C_1$–$C_6$alkoxy, $C_1$–$C_4$haloalkoxy, $C_1$–$C_6$alkylthio or $C_1$–$C_6$haloalkylthio groups;

$R_8$, $R_9$, $R_{13}$ and $R_{14}$ are each independently hydrogen, $C_1$–$C_6$alkyl, $C_1$–$C_6$alkylcarbonyl or
phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups;

$R_{10}$ and $R_{11}$ are each independently hydrogen, $C_1$–$C_6$alkyl or $C_1$–$C_6$haloalkyl;

$R_1$ and $R_2$ are each independently hydrogen, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_2$–$C_6$alkoxyalkyl, $(CH_2)_vC(O)R_{12}$,
$C_1$–$C_6$alkyl optionally substituted with one phenoxy or phenyl group wherein the phenyl ring of each group is independently, optionally substituted with from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups,
phenyl optionally substituted with from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, or
a 5- or 6-membered heteroaromatic ring optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, and
when $R_1$ and $R_2$ are taken together with the atom to which they are attached they may form a $C_3$–$C_6$cycloalkyl ring wherein $R_1R_2$ is represented by: —$(CH_2)_t$— where t is 2, 3, 4 or 5;

m, q and v are each independently 0, 1 or 2;

$R_{12}$ is hydrogen, $C_1$–$C_6$alkyl, $C_1$–$C_6$haloalkyl, $C_1$–$C_6$alkoxy, $C_1$–$C_6$haloalkoxy, $C_1$–$C_6$alkylthio, $C_1$–$C_6$haloalkylthio or $NR_{13}R_{14}$;

$R_3$ is hydrogen, $C_1$–$C_6$alkyl, $C_1$–$C_6$haloalkyl or $C(O)R_{15}$;

$R_{15}$ is $C_1$–$C_6$alkyl, $C_1$–$C_6$haloalkyl, $C_1$–$C_6$alkoxy or $C_1$–$C_6$haloalkoxy; and $R_5$ is $C_1$–$C_6$alkyl,
phenyl optionally substituted with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups, or
benzyl optionally substituted on the phenyl ring with any combination of from one to three halogen, $C_1$–$C_6$alkyl, $C_1$–$C_6$haloalkyl, $C_1$–$C_6$alkoxy, $C_1$–$C_6$haloalkoxy, $C_1$–$C_6$alkylthio or $C_1$–$C_6$haloalkylthio groups; and the optical isomers thereof and the agriculturally acceptable salts thereof, provided that: (1) R is other than $CO_2R_{10}$ when R is on the ortho-position of the phenyl ring, and (2) $R_2$ is other than ethyl or unsubstituted phenyl when X is O, n and p are 0 and $R_1$ is methyl.

* * * * *